(12) United States Patent
Fukuma et al.

(10) Patent No.: US 11,013,401 B2
(45) Date of Patent: May 25, 2021

(54) OPHTHALMOLOGIC APPARATUS

(71) Applicant: Topcon Corporation, Tokyo (JP)

(72) Inventors: Yasufumi Fukuma, Saitama (JP);
Hideharu Suzuki, Tokyo (JP);
Zhenguo Wang, Ridgewood, NJ (US);
Kazuhiro Oomori, Tokyo (JP);
Makoto Fujino, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 213 days.

(21) Appl. No.: 16/200,676

(22) Filed: Nov. 27, 2018

(65) Prior Publication Data

US 2020/0163545 A1    May 28, 2020

(51) Int. Cl.
| | | |
|---|---|---|
| *A61B 3/10* | (2006.01) | |
| *A61B 3/00* | (2006.01) | |
| *A61B 5/00* | (2006.01) | |
| *A61B 3/14* | (2006.01) | |
| *A61B 3/117* | (2006.01) | |

(52) U.S. Cl.
CPC ............ *A61B 3/101* (2013.01); *A61B 3/0041* (2013.01); *A61B 3/117* (2013.01); *A61B 3/14* (2013.01); *A61B 5/0071* (2013.01)

(58) Field of Classification Search
CPC .. A61B 3/102; A61B 3/14; A61B 3/12; A61B 3/0008; A61B 3/1005; A61B 3/107; A61B 3/117; A61B 3/13; A61B 5/14555; A61B 3/158
USPC .......................... 351/206, 246, 221, 212, 205
See application file for complete search history.

(56) References Cited

U.S. PATENT DOCUMENTS

| | | | |
|---|---|---|---|
| 2005/0162611 A1 | 7/2005 | Miwa | |
| 2015/0085252 A1 | 3/2015 | Fujimura et al. | |
| 2015/0374232 A1* | 12/2015 | Yoshino | A61B 3/12 351/206 |

FOREIGN PATENT DOCUMENTS

| | | | |
|---|---|---|---|
| JP | H09-289970 A | 11/1997 | |
| JP | 2001-309889 A | 11/2001 | |
| JP | 2005-211173 A | 8/2005 | |
| JP | 2017-136212 A | 8/2017 | |

* cited by examiner

*Primary Examiner* — Hung X Dang
(74) *Attorney, Agent, or Firm* — Xsensus LLP

(57) ABSTRACT

An ophthalmologic apparatus of some exemplary embodiments includes an illumination system, interference photographing system, anterior eye segment photographing system, first optical path coupling element, and controller. The illumination system projects illumination light output from a light source, onto the anterior eye segment of a subject's eye. The interference photographing system performs photographing of an interference pattern formed on the cornea by the illumination light. The anterior eye segment photographing system performs photographing of the anterior eye segment onto which the illumination light is being projected. The first optical path coupling element couples the optical path of the interference photographing system and the optical path of the anterior eye segment photographing system with one another. The controller controls a display device to display an interference image acquired by the interference photographing system, over an anterior eye segment image acquired by the anterior eye segment photographing system.

13 Claims, 7 Drawing Sheets

OPHTHALMOLOGIC APPARATUS

FIELD

The present invention relates to an ophthalmologic apparatus for examining the state of tears of a subject's eye.

BACKGROUND

In recent years, patients with dry eye syndrome are increasing. The causes of this are believed to be abusing of eyes due to work performed using a display of a computer or the like (VDT work), drying of air by cooling and/or heating, wearing of a contact lens, and the like.

The most common method of testing for dry eye syndrome is the Schirmer test, which measures the amount of tears. In addition, observation of the cornea stained with fluorescein using a slit lamp microscope and an examination for measuring the stability of the tear film (tear film breakup time (BUT) examination) are also being employed.

The followings are known apparatuses for examining dry eye syndrome. Japanese Unexamined Patent Application Publication No. 1997-289970 discloses an ophthalmologic apparatus in which a light projection system is disposed so that light rays are substantially perpendicularly incident on the corneal surface and a diaphragm having substantially the same size as the exit pupil diameter of the specular reflection light is disposed in the vicinity of the exit pupil, thereby effectively acquiring the specular reflection light from the anterior eye segment of the subject's eye.

Japanese Unexamined Patent Application Publication No. 2001-309889 discloses an ophthalmologic apparatus that performs color photography of an interference pattern formed by the tear film to acquire time-series images and obtains a time-dependent change in the hue of the interference pattern from the time-series images, thereby carrying out an examination of the state of the tear film in an objective manner.

Japanese Unexamined Patent Application Publication No. 2005-211173 discloses an ophthalmologic apparatus that performs color photography of an interference pattern formed by the tear film to acquire an image and analyzes the interference pattern for each color component of the image to evaluate the degree of progress of dry eye syndrome, thereby quantifying the degree of progress of dry eye syndrome with high precision and high accuracy.

Japanese Unexamined Patent Application Publication No. 2017-136212 discloses an ophthalmologic apparatus that processes a plurality of front images obtained by successive photography of the anterior eye segment of the subject's eye to evaluate the location and shape of a dry spot and the movement direction of tears around the dry spot, thereby evaluating the type of dry eye syndrome in an objective manner.

As disclosed in Japanese Unexamined Patent Application Publication No. 2017-136212, one of the important items in dry eye syndrome evaluation is the locations of dry spots (more generally, the distribution of the thicknesses of tears or the distribution of the state abnormalities of tears). As a matter of course, it is unknown in which part of the anterior eye segment an abnormality will have occurred before the examination. Therefore, it is desirable for an examiner to be able to observe a wide area of the anterior eye segment in order not to overlook the abnormalities occurring in the periphery or edge of the cornea as well as in order to improve the efficiency of the examination.

Further, in the case of presenting examination results, it is desirable to display the locations or distribution of abnormalities over the anterior eye segment image so that the examiner can easily (intuitively) find the abnormal areas in the anterior eye segment. This anterior eye segment image is desired to be an image of a wide area in the anterior eye segment.

Furthermore, taking into consideration the possibility of occurrence of misregistration between the interference pattern image and the anterior eye segment image due to eye movements or body movements, is desirable to perform photographing of the interference pattern for obtaining the locations or distribution of abnormalities and photographing of the anterior eye segment for obtaining an anterior eye segment image, at almost the same time.

SUMMARY

The following presents a simplified summary of the innovation in order to provide a basic understanding of some aspects described herein. This summary is not an extensive overview of the claimed subject matter. It is intended to neither identify key or critical elements of the claimed subject matter nor delineate the scope of the subject innovation. Its sole purpose is to present some concepts of the claimed subject matter in a simplified form as a prelude to the more detailed description that is presented later.

An ophthalmologic apparatus according to some aspects includes an illumination system, an interference photographing system, an anterior eye segment photographing system, a first optical path coupling element, and a controller. The illumination system is configured to project illumination light output from a light source, onto the anterior eye segment of a subject's eye. The interference photographing system is configured for photographing an interference pattern formed on the cornea by the illumination light. The anterior eye segment photographing system is configured for photographing the anterior eye segment onto which the illumination light is being projected. The first optical path coupling element couples the optical path of the interference photographing system and the optical path of the anterior eye segment photographing system with one another. The controller is configured to control a display device to display an interference image acquired by the interference photographing system, over an anterior eye segment image acquired by the anterior eye segment photographing system.

According to some aspects, it is possible to present the parts where abnormalities of the state of tears have occurred over a wide area in the anterior eye segment with good locational precision.

The following description and the annexed drawings set forth in detail certain illustrative aspects of the claimed subject matter. These aspects are indicative, however, of but a few of the various ways in which the principles of the innovation may be employed and the claimed subject matter is intended to include all such aspects and their equivalents. Other advantages and novel features of the claimed subject matter will become apparent from the following detailed description of the innovation in view of the drawings.

DETAILED DESCRIPTION

Figure 1:
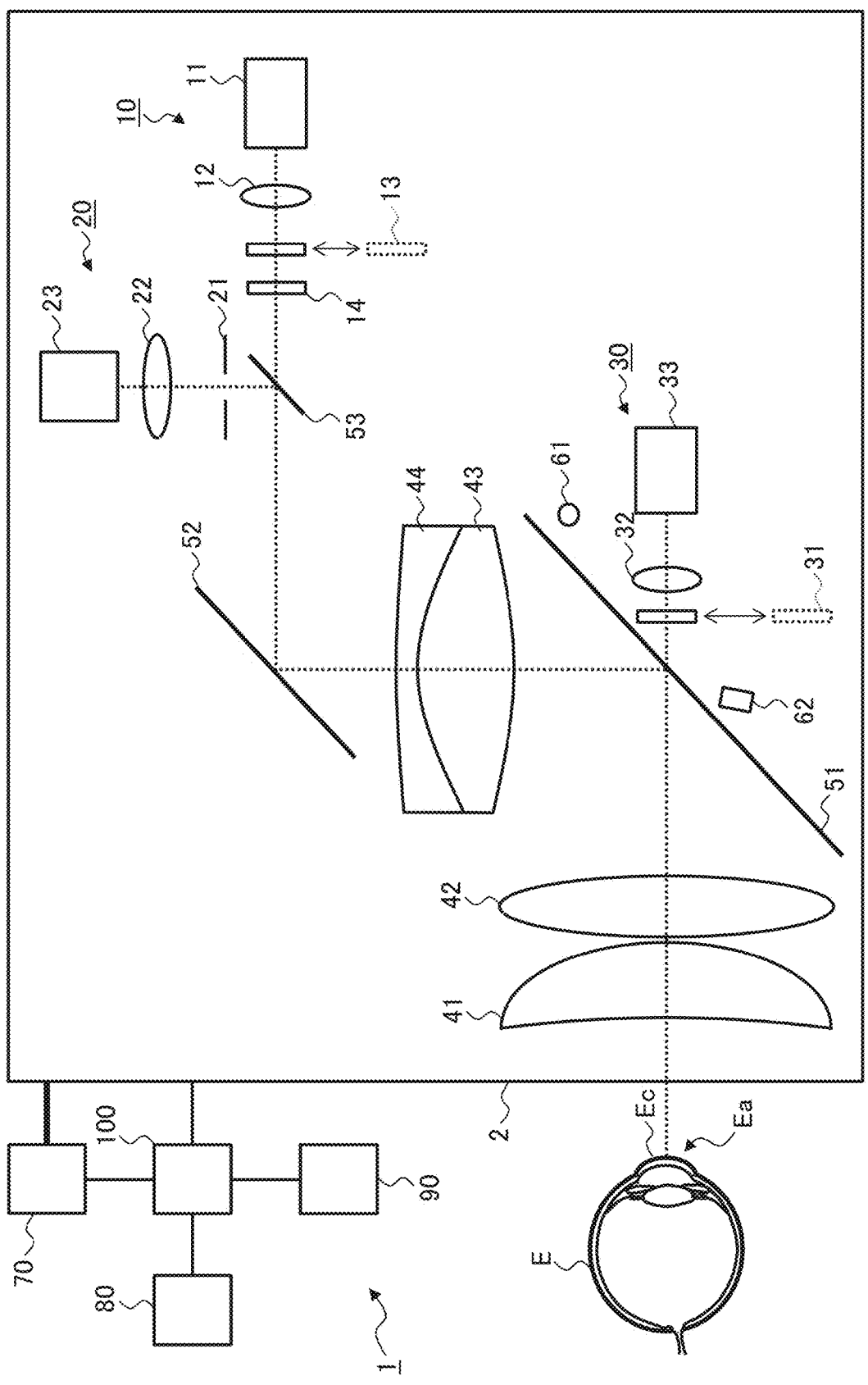
FIG. 1 is a schematic diagram illustrating an example of the configuration of an ophthalmologic apparatus according to an exemplary embodiment.

A purpose of some exemplary embodiments is to make it possible to present the parts where abnormalities of the state of tears have occurred over a wide area in the anterior eye segment with good locational precision.

An ophthalmologic apparatus according to the first aspect of some exemplary embodiments includes an illumination system, an interference photographing system, an anterior eye segment photographing system, a first optical path coupling element, and a controller. The illumination system is configured to project illumination light output from a light source, onto the anterior eye segment of a subject's eye. The interference photographing system is configured for photographing an interference pattern formed on the cornea by the illumination light. The anterior eye segment photographing system is configured for photographing the anterior eye segment onto which the illumination light is being projected. The first optical path coupling element couples the optical path of the interference photographing system and the optical path of the anterior eye segment photographing system with one another. The controller is configured to control a display device to display an interference image acquired by the interference photographing system, over an anterior eye segment image acquired by the anterior eye segment photographing system.

The second aspect of some exemplary embodiments is the ophthalmologic apparatus of the first aspect and further includes a first lens group disposed in a position between the subject's eye and the first optical path coupling element and a second lens group disposed in a position on an opposite side of the subject's eye with respect to the first optical path coupling element. The combination of the first lens group and the second lens group functions as an objective lens of the interference photographing system. In addition, the first lens group functions as an objective lens of the anterior eye segment photographing system.

The third aspect of some exemplary embodiments is the ophthalmologic apparatus of the second aspect in which a lens located closest to the first optical path coupling element among lenses included in the anterior eye segment photographing system is disposed at the focal position of the first lens group or in a vicinity thereof.

The fourth aspect of some exemplary embodiments is the ophthalmologic apparatus of any of the first to third aspects and further includes a second optical path coupling element that couples the optical path of the illumination system and the optical path of the interference photographing system with one another.

The fifth aspect of some exemplary embodiments is the ophthalmologic apparatus of the fourth aspect in which each of the first optical path coupling element and the second optical path coupling element is a beam splitter. In addition, returning light of the illumination light for photographing the interference pattern, is reflected by each of the first optical path coupling element and the second optical path coupling element and guided to an image sensor provided in the interference photographing system.

The sixth aspect of some exemplary embodiments is the ophthalmologic apparatus of any of the first to fifth aspects and further includes an illumination intensity changing device that changes the intensity of the illumination light projected onto the anterior eye segment.

The seventh aspect of some exemplary embodiments is the ophthalmologic apparatus of any of the first to sixth aspects and further includes an excitation filter and a barrier filter. The excitation filter is configured to generate excitation light for a fluorescent agent administered to the anterior eye segment, from the illumination light. The barrier filter is configured to selectively pass fluorescence emitted from the fluorescent agent that has absorbed the excitation light.

The eighth aspect of some exemplary embodiments is the ophthalmologic apparatus of any of the first to seventh aspects and further includes a projection system, a detection system, and a first alignment device. The projection system is configured to project alignment light onto the anterior eye segment along a direction non-parallel to the optical axis of the optical path from the first optical path coupling element toward the subject's eye. The detection system is configured to detect reflected light of the alignment light from the anterior eye segment. The first alignment device is configured to perform alignment in the direction along the optical axis, based on an output from the detection system.

The ninth aspect of some exemplary embodiments is the ophthalmologic apparatus of the eighth aspect in which the projection system includes an alignment light source that outputs the alignment light and the detection system includes an image sensor that detects the reflected light. In addition, each of the alignment light source and the image sensor is disposed in a position on the opposite side of the subject's eye with respect to the first optical path coupling element.

The tenth aspect of some exemplary embodiments is the ophthalmologic apparatus of any of the first to ninth aspects and further includes a second alignment device. The second alignment device is configured to perform alignment in a direction perpendicular to the optical axis of the optical path from the first optical path coupling element toward the subject's eye, based on an anterior eye segment image acquired by the anterior eye segment photographing system.

The eleventh aspect of some exemplary embodiments is the ophthalmologic apparatus of any of the first to seventh aspects and further includes two or more photographing devices and a third alignment device. The two or more photographing devices are configured to photograph the anterior eye segment from directions different from each other. The third alignment device is configured to perform three dimensional alignment based on two or more photographed images respectively acquired by the two or more photographing devices.

An ophthalmologic apparatus according to some exemplary embodiments will be described in detail below with referring to the drawings.

First, the outline of the embodiment will be described. The ophthalmologic apparatus of the embodiment is configured to acquire an interference image by photographing an interference pattern representing the state of the tears on the cornea, acquire an anterior eye segment image by photographing the anterior eye segment, and overlay the interference image on the anterior eye segment image. At least part of the element group for interference photographing (i.e., at least part of the interference photographing system) is different from the element group for anterior eye segment photographing (i.e., the anterior eye segment photographing system).

The presented interference image may be an interference image itself (a raw image) acquired by the interference photographing system, or an interference image (a processed image) obtained by processing the raw image. The processed image may be, for example, a color map that represents a parameter distribution obtained from a raw image in pseudo colors, or a map that represents a region where parameter values belong to a predetermined range. This parameter may be, for example, the thickness of any one of the lipid layer, the aqueous layer and the mucinous layer of the tear film, the thickness of any two layers, or the thickness of the three layers. Further, the processed image may be created by applying any kind of image processing such as correction, adjustment or enhancement, to the raw image.

Likewise, the presented anterior eye segment image may be an anterior eye segment image itself (a raw image) acquired by the anterior eye segment photographing system, or an anterior eye segment image (a processed image) obtained by processing the raw image. The processed image may be created by applying any kind of image processing such as correction, adjustment or enhancement, to the raw image, for example.

The display device on which the interference image and the anterior eye segment image are displayed may be a part of the ophthalmologic apparatus according to the embodiment, or may not. In the latter case, the display device is a peripheral device of the ophthalmologic apparatus according to the embodiment.

In the present specification, unless otherwise mentioned, "image data" and an "image" based on the image data are not distinguished from each other. Likewise, a site or a tissue of the subject's eye and an image representing the site or the tissue are not distinguished from each other, unless otherwise mentioned.

Further, in the present specification, unless otherwise mentioned, a "lens" refers to a single lens or a combination of two or more lenses. Likewise, unless otherwise mentioned, a "lens group" refers to a collection of two or more lenses or a single lens.

In addition, In the present specification, the term "processor" is used to mean, for example, a circuitry or a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or other circuitry or circuit. The processor realizes the functions according to the embodiment, for example, by reading out and executing a program stored in a storage circuit or a storage device.

<Configuration>

Figure 2:
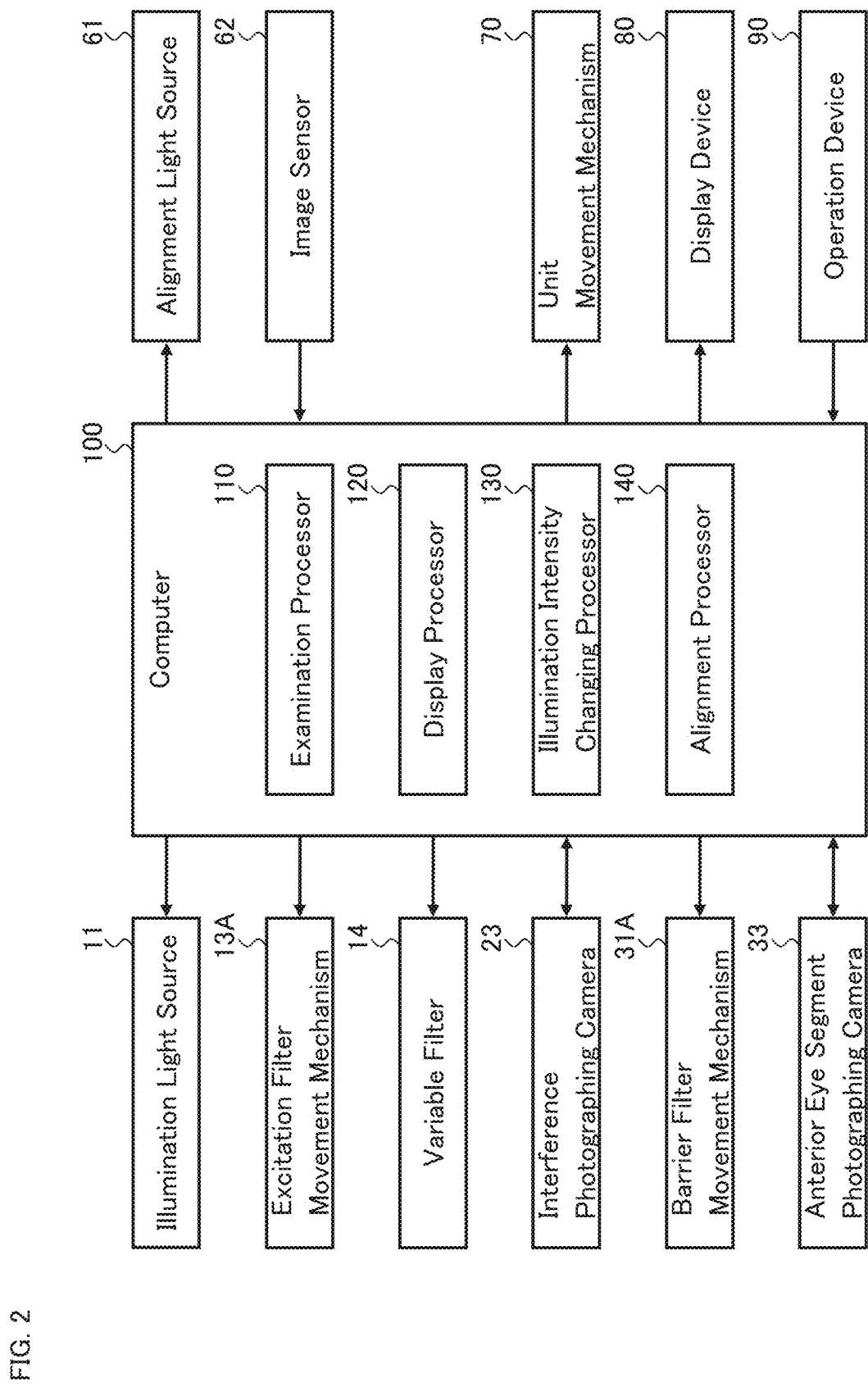
FIG. 2 is a schematic diagram illustrating an example of the configuration of the ophthalmologic apparatus according to the exemplary embodiment.

FIG. 1 and FIG. 2 show an example of the configuration of the ophthalmologic apparatus according to the embodiment. The ophthalmologic apparatus 1 has following functions: a function of photographing an interference pattern representing the state of tears on the cornea Ec of the subject's eye E; a function of photographing the anterior eye segment Ea; and a function of presenting an interference image representing the interference pattern over an anterior eye segment image.

As an exemplary configuration for realizing these functions, the ophthalmologic apparatus 1 includes the examination unit 2, the unit movement mechanism 70, the display device 80, the operation device 90, and the computer 100. The computer 100 may be, for example, an embedded system of the ophthalmologic apparatus 1.

The examination unit 2 stores various kinds of optical systems and various kinds of mechanisms. The exemplary examination unit 2 includes the illumination system 10, the interference photographing system 20, the anterior eye segment photographing system 30, the first lens group including the two lenses 41 and 42, the second lens group including the two lenses 43 and 44, the optical path coupling element 51, the reflection mirror 52, the optical path coupling element 53, the alignment light source 61, and the image sensor 62.

The illumination system 10 is configured to project illumination light onto the anterior eye segment Ea of the subject's eye E. The exemplary illumination system 10 includes the illumination light source 11, the collimator lens 12, the excitation filter 13, and the variable filter 14. The optical path of the illumination system 10 is formed by the illumination light source 11, the collimator lens 12, the excitation filter 13, the variable filter 14, (the optical path coupling element 53,) the reflection mirror 52, the lens 44, the lens 43, the optical path coupling element 51, the lens 42, and the lens 41.

The illumination light source 11 emits the illumination light. The operation of the illumination light source 11 is controlled by the computer 100.

The collimator lens 12 converts the illumination light output from the illumination light source 11 into a parallel light beam. The collimator lens 12 consists of, for example, a single lens or a combination of two or more lenses.

The excitation filter 13 is placed in the optical path (as shown by the solid line) when the modality of the anterior eye segment photographing is set to fluorescent contrast photographing, and is placed outside the optical path (as shown by the dotted line) in other cases. The movement of the excitation filter 13 is performed by the excitation filter movement mechanism 13A. The excitation filter movement mechanism 13A includes an actuator that operates in accordance with a command issued from the computer 100. The actuator may be, for example, a solenoid actuator.

In fluorescent contrast photographing, a fluorescent agent (a fluorescent dye) is administered to the anterior eye segment Ea. The excitation filter 13 generates excitation light for the fluorescent agent from the illumination light. More specifically, the excitation filter 13 selectively passes the wavelength that excites the fluorescent agent. In a typical example, the fluorescent dye is fluorescein and the transmitting center wavelength of the excitation filter 13 is set at the absorption maximum wavelength of fluorescein of 494 nm, or near the absorption maximum wavelength (e.g., at a wavelength within the range from 490 nm to 500 nm).

The variable filter 14 is an optical element for changing the intensity (light amount) of the illumination light projected onto the subject's eye E. Since it takes a certain amount of time (e.g., 10 seconds or more) to evaluate the time-dependent change of the interference pattern caused by tears, it is considered desirable to be capable of regulating the intensity of the illumination light so that the subject is able to have his/her eyes open during the entire period of time. The variable filter 14 is an example of elements to realize such a request.

The variable filter 14 may include, for example, one or both of a neutral density filter (ND filter) and a band pass filter (BPF). The variable filter 14 includes a single filter or two or more filters.

When the variable filter 14 consists of a single filter, the variable filter 14 is, for example, an optical filter whose filter characteristic (e.g., transmission characteristic, absorption characteristic) can vary in a continuous or discrete manner. The computer 100 performs control for hanging the filter characteristic.

When the variable filter 14 includes two or more filters, these filters are selectively placed in the optical path. As a typical example of this case, the variable filter 14 includes two or more filters mounted in a turret and an actuator that moves (typically rotates) the turret. The actuator may be, for example, a pulse motor operated by a command (pulse control signal) issued from the computer 100.

Note that the intensity of the illumination light projected onto the subject's eye E can be changed without using the variable filter 14. For example, some exemplary embodiments may be configured to vary one or both of the intensity and the wavelength band of the illumination light output by the illumination light source (11), to change the intensity of the illumination light projected onto the subject's eye E. Further, some exemplary embodiments may be configured to change the intensity of the illumination light projected onto the subject's eye E, by means of a combination of the illumination light source control and the variable filter control.

Further, one or more of the two or more filters provided in the variable filter 14 may be the excitation filter 13. In the case where the excitation filter 13 is included in the variable filter 14, the computer 100 controls the variable filter 14 to perform insertion and removal of the excitation filter 13 into and from the optical path when the fluorescent contrast photographing is carried out.

According to the illumination system 10 of the present example, the illumination light output from the illumination light source 11 is converted into a parallel light beam by the collimator lens 12. When applying the fluorescent contrast photographing, the illumination light that has passed through the collimator lens 12 becomes excitation light by the excitation filter 13, and the intensity of the excitation light is regulated by the variable filter 14. When applying a modality other than the fluorescent contrast photographing, the intensity of the illumination light that has passed through the collimator lens 12 is regulated by the variable filter 14. The illumination light (the excitation light) that has passed through the variable filter 14 further passes through the optical path coupling element 53, the reflection mirror 52, the lens 44, the lens 43, the optical path coupling element 51, the lens 42, and the lens 41, and then is projected onto the anterior eye segment Ea.

The interference photographing system 20 is configured to photograph an interference pattern formed on the cornea by the illumination light projected onto the anterior eye segment Ea by the illumination system 10. The interference pattern is formed by the illumination light being reflected at layers (layer boundaries) of the tear film. For example, the reflected light from the front surface of the lipid layer of the tear film and the reflected light from the back surface interfere with each other, whereby a pattern corresponding to the distribution of the thicknesses of the lipid layer is formed.

The interference photographing system 20 includes the diaphragm 21, the telecentric lens 22, and the interference photographing camera 23. The optical path of the interference optical system 20 is formed by the lens 41, the lens 42, the optical path coupling element 51, the lens 43, the lens 44, the reflection mirror 52, the optical path coupling element 53, the diaphragm 21, the telecentric lens 22, and the interference photographing camera 23.

The diaphragm 21 is an optical element for limiting (regulating) the amount of light guided to the interference photographing camera 23. The diaphragm 21 may be a variable diaphragm controlled by the computer 100.

The telecentric lens 22 may be, for example, an image-space telecentric lens. By employing an image-space telecentric lens, light rays are incident on the entire photo-detection surface of the interference photographing camera 23 in a substantially perpendicular manner. This can lead to the elimination of roll-off and vignetting, and further lead to the equalization of the peripheral light amount ratio. The telecentric lens 22 consists of, for example, a single lens or a combination of two or more lenses.

The interference photographing camera 23 detects the light that has passed through the telecentric lens 22 and generates an image (an interference image) representing the interference pattern formed on the cornea. The interference photographing camera 23 has sensitivity at least in the visible spectrum. The interference photographing camera 23 may be, for example, a color video camera, typically a three-CCD video camera, or a three-CMOS video camera. Such a configuration enables to obtain various color components of the interference image.

The reflected light of the illumination light projected onto the anterior eye segment Ea by the illumination system 10, passes through the lens 41, the lens 42, the optical path coupling element 51, the lens 43, the lens 44, the reflection mirror 52, the optical path coupling element 53, the diaphragm 21 and the telecentric lens 22, and then is incident onto the interference photographing camera 23.

The anterior eye segment photographing system 30 is configured to photograph the anterior eye segment Ea onto which the illumination light is projected by the illumination system 10. The anterior eye segment photographing system 30 includes the barrier filter 31, the lens 32, and the anterior eye segment photographing camera 33. The optical path of the anterior eye segment photographing system 30 is formed by the lens 41, the lens 42, (the optical path coupling element 51,) the barrier filter 31, the lens 32, and the anterior eye segment photographing camera 33.

The barrier filter 31 is placed in the optical path (in the state shown by the solid line) when the modality of the anterior eye segment photographing is set to the fluorescent contrast photographing, and is placed outside the optical path (in the state shown by the dotted line) in other cases. The movement of the barrier filter 31 is performed by the barrier filter movement mechanism 31A. The barrier filter movement mechanism 31A includes an actuator that operates in accordance with a command issued from the computer 100. The actuator may be, for example, a solenoid actuator.

The computer 100 executes synchronous control of the operation of the excitation filter movement mechanism 13A and the operation of the barrier filter movement mechanism 31A. More specifically, when the modality of the anterior eye segment photographing is set to the fluorescent contrast photographing, the computer 100 controls the excitation filter movement mechanism 13A and the barrier filter movement mechanism 31A so that both the excitation filter 13 and the barrier filter 31 are placed in the respective optical paths. In addition, when the modality of the anterior eye segment photographing is set to a modality other than the fluorescent contrast photographing, the computer 100 controls the excitation filter movement mechanism 13A and the barrier filter movement mechanism 31A so that both the excitation filter 13 and the barrier filter 31 are placed outside the respective optical paths.

In the fluorescent contrast photographing, the fluorescent agent (the fluorescent dye) administered to the anterior eye segment Ea absorbs the excitation light generated by the excitation filter 13 and emits fluorescence of a specific wavelength. The barrier filter 31 selectively passes the wavelength of the fluorescence. As a typical example, when the fluorescent dye is fluorescein, the transmitting center wavelength of the barrier filter 13 is set at the emission maximum wavelength of fluorescein of 521 nm, or near the emission maximum wavelength.

The lens 32 is, for example, an imaging lens that forms an image on the photo-detection surface of the anterior eye segment photographing camera 33. Alternatively, as with the interference photographing system 20, the lens 32 may be a telecentric lens (an image-space telecentric lens). The lens 32 consists of, for example, a single lens or a combination of two or more lenses.

A lens located closest to the optical path coupling element 51 among the lenses 32 is disposed at the focal position of the first lens group consisting of the two lenses 41 and 42, or in the vicinity of the focal position. When the lens 32 consists of a single lens, the lens 32 is disposed at or near the back focal position of the first lens group. When the lens 32 consists of two or more lenses, the lens closest to the optical path coupling element 51 among the two or more lenses, that is, the lens located closest to the subject's eye E, is disposed at or near the back focal position of the first lens group. With such an arrangement, the field of view of the anterior eye segment photographing camera 33 can be widened to capture a wide area of the anterior eye segment Ea.

The anterior eye segment photographing camera 33 photographs the anterior eye segment Ea by detecting the light that has passed through the lens 32. This acquires an anterior eye segment image. The anterior eye segment photographing camera 33 has sensitivity at feast in the wavelength range for the fluorescent contrast photographing. For example, the anterior eye segment photographing camera 33 has sensitivity in the visible spectrum and the infrared spectrum. The anterior eye segment photographing camera 33 may be, for example, a color video camera or a monochrome video camera, and may typically be a CCD video camera, a three-CCD video camera, a CMOS video camera, or a three-CMOS video camera.

The first lens group consisting of the two lenses 41 and 42 is disposed in a position between the subject's eye E and the optical path coupling element 51. The second lens group consisting of the two lenses 43 and 44 is disposed in a position on the opposite side of the subject's eye E with respect to the optical path coupling element 51. In other words, the second lens group is disposed in a position between the interference photographing camera 23 and the optical path coupling element 51.

For example, the surface of the lens 41 on the side of the subjects eye E (the front surface) is formed in a concave shape or a planar shape, and the surface opposite to the subject's eye E (the back surface) is formed in a convex aspherical shape. As for the lens 42, for example, both the front surface and the back surface are formed in a convex shape or a planar shape.

The lens 43 and the lens 44 form a cemented lens (doublet). The lens 43 is formed in a convex shape on both the front surface and the back surface, for example. As for the lens 44, for example, both the front surface and the back surface formed in a concave shape.

Such a lens configuration is designed to satisfy the following two conditions: (1) the illumination light is incident substantially perpendicular to each position on the cornea Ec; (2) the reflected light from each position on the cornea Ec travels, up to the lens 41, through the route substantially the same as the path of the illumination light incident on the concerned position in the opposite direction, and then is detected by the interference photographing system 20.

Figure 3:
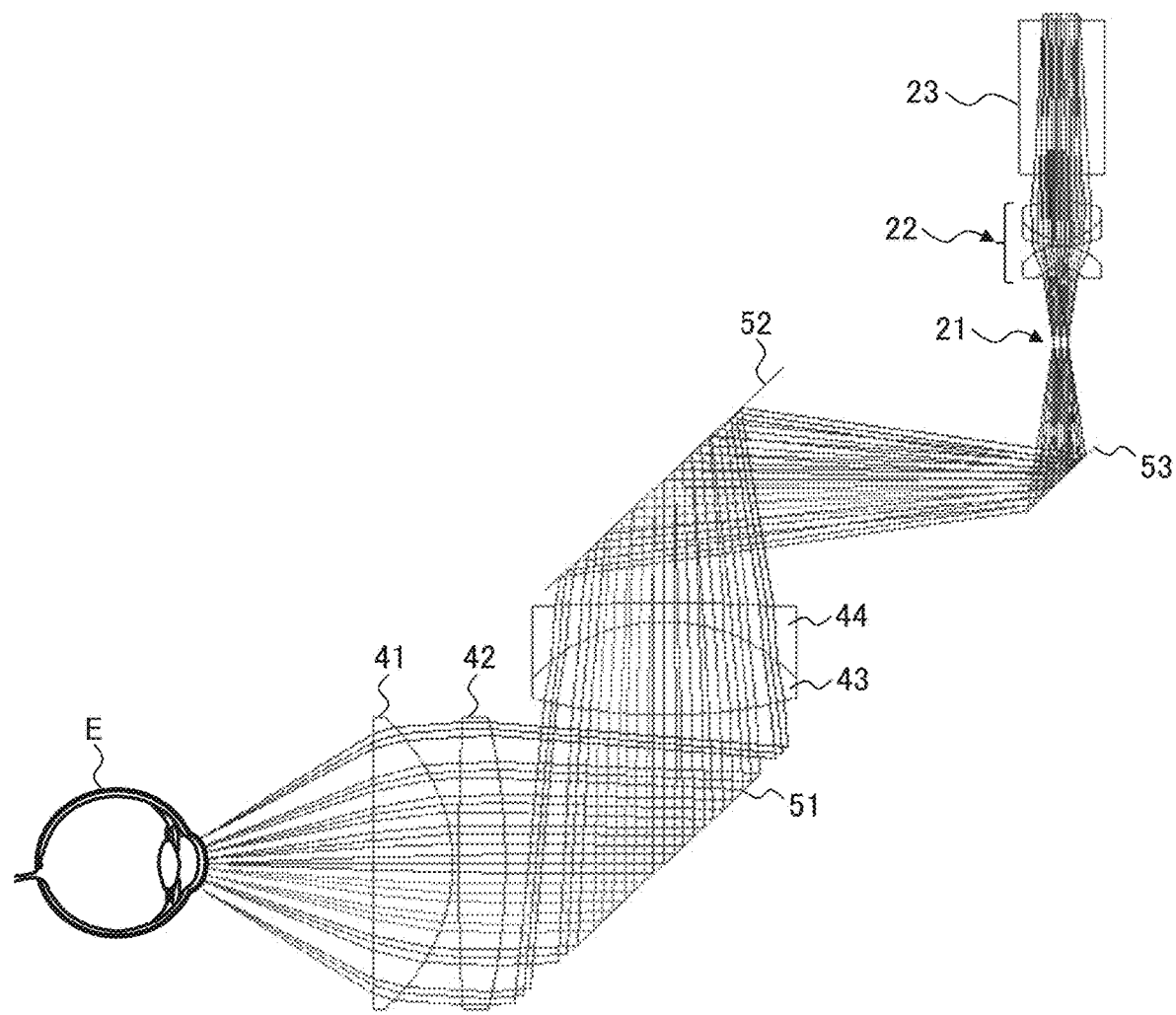
FIG. 3 is a schematic diagram for describing an example of the configuration of the ophthalmologic apparatus according to the exemplary embodiment.

It can be seen from the light ray diagram (diagram of a simulation result) of FIG. 3, that the interference photographing system 20 according to the present example satisfies the above two conditions. Incidentally, although there is some description relating to the two conditions in Japanese Unexamined Patent Application Publication No. 1997-289970, no specific and concrete optical system that actually satisfies the two conditions has been disclosed in known literatures, and it is thought that the present inventors have devised such an optical system for the first time.

By applying the optical system that satisfies the above two conditions, the path of the illumination light corresponding to each position on the cornea Ec and the path of the reflected light thereof substantially coincide with each other. As a result of this, the distribution of the state of tears on the curved surface of the cornea Ec, can be grasped accurately from the directions each perpendicular to the curved surface.

Configurations for satisfying the aforementioned two conditions are not limited to the above. As a result of earnest research, the inventors have found out that at least each of the following optical system configurations (A) to (C) satisfies the above two conditions. Note that these are merely examples, and any modification (omission, substitution, addition, etc.) is permissible.

(A) In an optical system configuration of the present example, the following three lenses may be used in place of the four lenses 41 to 44 shown in FIG. 1. The first lens closest to the subject's eye has the front surface formed in a concave shape and the back surface formed in a convex aspherical shape. The second lens adjacent to the first lens is formed in a convex shape on both the front surface and the back surface. The third lens, the front surface of which is affixed to the back surface of the second lens, has the front surface formed in a concave shape and the back surface formed in a convex shape.

(B) In an optical system configuration of the present example, the following four lenses may be used in place of the four lenses 41 to 44 shown in FIG. 1. The first lens closest to the subject's eye has the front surface formed in a gentle convex shape or a planar shape, and the back surface formed in a convex aspherical shape. The second lens second-closest to the subject's eye after the first lens is formed in a convex shape on both the front surface and the back surface. The third lens, the front surface of which is affixed to the back surface of the second lens, has the front surface formed in a concave shape and the back surface formed in a convex shape. The fourth lens, the front surface of which faces the back surface of the third lens, has the front surface formed in a convex shape and the back surface formed in a concave shape.

(C) In an optical system configuration of the present example, the following five lenses may be used in place of the four lenses 41 to 44 shown in FIG. 1. The first lens closest to the subject's eye has the front surface formed in a planar shape or a concave shape, and the back surface formed in a convex aspherical shape. The second lens adjacent to the first lens has the front surface formed in a planar shape and the back surface formed in a convex shape. The third lens adjacent to the second lens is formed in a convex shape on both the front surface and the back surface. The fourth lens, the front surface of which is affixed to the back surface of the third lens, has the front surface formed in a concave shape and the back surface formed in a convex shape. The fifth lens adjacent to the fourth lens has the front surface formed in a convex shape and the back surface in a concave shape.

In the example shown in FIG. 1, the four lenses 41, 42, 43 and 44, that is, the first lens group and the second lens group, function as an objective lens of the interference photographing system 20. Further, the two lenses 41 and 42, that is, the first lens group, function as an objective lens of the anterior eye segment photographing system 30.

According to such a configuration, as to the interference photographing system 20, the illumination light can be made incident substantially perpendicularly to each position on the cornea Ec, and the reflected light from each position on the cornea Ec can be directed to travel along substantially the same route as the incident path. In addition, as to the anterior eye segment photographing system 30, a wide field of view can be secured, that is, a wide area of the anterior eye segment Ea can be imaged.

The light detected by the interference photographing system 20 and the light detected by the anterior eye segment photographing system 30 are both returning lights from the anterior eye segment Ea, but different from each other. Those skilled in the art will appreciate that it is not easy to configure an optical system capable of detecting such different lights separately by means of individual optical systems configured to satisfy requirements different from each other.

The optical path coupling element 51 is an optical element that couples the optical path of the interference photographing system 20 and the optical path of the anterior eye segment photographing system 30. For example, the optical path coupling element 51 couples the optical path of the interference photographing system 20 and the optical path of the anterior eye segment photographing system 30 in a coaxial manner (In other words, the optical path coupling element 51 couples the optical paths in the way that their optical axes intersect each other).

The optical path coupling element 51 may be any type of beam splitter. In the present example, a half mirror can be used as the optical path coupling element 51 since the interference photographing system 20 uses broadband visible light and the anterior eye segment photographing system 30 uses visible fluorescence (fluorescein). Further, in the example shown in FIG. 1, the optical path coupling element 51 also has a function of coupling the optical path of the illumination system 10 and the optical path of the anterior eye segment photographing system 30.

In some exemplary embodiments, a dichroic mirror can be used as the optical path coupling element 51 when adopting a configuration that separates the passing light (transmitted light) and the reflected light in terms of wavelengths. In some other exemplary embodiments, a polarization beam splitter can be used as the optical path coupling element 51 when adopting a configuration that separates the passing light (transmitted light) and the reflected light in terms of polarization. Note that these are merely illustrative examples of an element (first optical path coupling element) for coupling the optical path of the interference photographing system and the optical path of the anterior eye segment photographing system, and any modification (omission, substitution, addition, etc.) is allowable.

The reflection mirror 52 changes the direction of the optical path of the illumination system 10 and that of the optical path of the interference photographing system 20. This makes it possible to make the configuration of the optical system compact, and as a result, it becomes possible to downsize the ophthalmologic apparatus 1. It should be noted that any kind of elements and any kind of configurations can be employed for this purpose or other purposes. For example, the position, arrangement angle, number, size, etc. of the reflection mirror may be designed in an appropriate manner. Further, an element different from the reflection mirror may be used.

The optical path coupling element 53 is an optical element that couples the optical path of the illumination system 10 and the optical path of the interference photographing system 20. For example, the optical path coupling element 53 couples the optical path of the illumination system 10 and the optical path of the interference photographing system 20 in a coaxial manner.

The optical path coupling element 53 may be any type of beam splitter. In the present example, a half mirror can be used as the optical path coupling element 53 since the illumination system 10 and the interference photographing system 20 both use broadband visible light. As with the optical path coupling element 51, a dichroic mirror, a polarizing beam splitter or another type of beam splitter can be adopted instead of a half mirror as needed.

In the example shown in FIG. 1, the light guided by the interference photographing system 20 (that is, the returning light of the illumination light for photographing the interference pattern caused by the tears on the cornea Ec) is guided via the two beam splitters and is reflected by the both beam splitters. More specifically, the light guided by the interference photographing system 20 is reflected by the optical path coupling element 51 and also reflected by the optical path coupling element 53, and directed to the interference photographing camera 23.

This configuration is intended to avoid disturbance of light as it passes through a beam splitter. The present configuration makes it possible to detect the interference pattern on the cornea Ec with high accuracy.

The alignment light source 61 and the image sensor 62 are used for alignment in the direction along the optical axis of the lens 41 (referred to as Z alignment in the Z direction). The alignment light source 61 projects light e.g., infrared light) for Z alignment onto the subject's eye E. The light output from the alignment light source 61 is projected in an oblique manner onto the cornea Ec via the lens 42 and the lens 41. The reflected light of the projected light at the cornea forms an image on the photo-detection surface of the image sensor 62 by the lens 41 and the lens 42 (as well as by other lenses not shown in the figures).

The image sensor 62 may be any type of one or two dimensional image sensor. In other words, the image sensor 62 provided in the Z alignment system may be any type of image sensor in which a plurality of light detecting elements (e.g., photodiodes) are arranged in one or two dimensional manner. The image sensor 62 is typically a line sensor.

In some exemplary embodiments, the light emitted by the alignment light source 61 and traveling toward the lens 42 passes through a notch, an aperture, or a light transmitting part formed in the optical path coupling element 51, for example, and then reaches the lens 42. Similarly, the light traveling from the lens 42 toward the image sensor 62 passes through a notch, an aperture, or a light transmitting part formed in the optical path coupling element 51, for example, and reaches image sensor 62. Such a configuration makes it possible to provide elements for alignment while satisfying the above-described conditions regarding the interference photographing system 20 and enlarging the field of view of the anterior eye segment photographing system 30.

The change in the position of the cornea Ec (e.g., the corneal apex) in the Z direction causes the change in the projection position of the light on the photo-detection surface of the image sensor 62. The computer 100 can determine the position of the cornea Ec (e.g., the corneal apex) based on the position at which the image sensor 62 has detected the light. Further, the computer 100 performs the Z alignment of the examination unit 2 by controlling the unit movement mechanism 70 based on the determined position of the cornea Ec (e.g., the corneal apex). The present Z alignment method is an example of optical-lever-based alignment techniques.

The unit movement mechanism 70 moves the examination unit 2 in a three dimensional manner. In a typical example, the unit movement mechanism 70 includes the followings: a Z stage that is movable in the Z direction (i.e., the front and back directions); a Z movement mechanism that moves the Z stage; an X stage that is movable in the X direction (i.e., the left and right directions or the horizontal direction) perpendicular to the Z direction; an X movement mechanism that moves the X stage; a Y stage that is movable in the Y direction (i.e., the up and down directions or the vertical direction) perpendicular to both the Z direction and the X direction; and a Y movement mechanism that moves the Y stage. Each of these movement mechanisms includes an actuator (e.g.; a pulse motor) that operates under the control of the computer 100.

The display device 80 functions as a part of the user interface device; and displays information under the control of the computer 100. The display device 80 may be, for example, a liquid crystal display (LCD) or an organic light emitting diode (OLED) display.

The operation device 90 functions as a part of the user interface device and is used for manually operating the ophthalmologic apparatus 1. The operation device 90 may include any kinds of hardware keys, such as a joystick, buttons, and switches, provided in the ophthalmologic apparatus 1. In addition, the operation device 90 may include any kinds of peripheral devices, such as a keyboard, a mouse, a joystick, and an operation panel, connected to the ophthalmologic apparatus 1. In addition, the operation device 90 may include any kinds of software keys, such as buttons, icons, and menus, displayed on the touch panel.

The computer 100 executes various kinds of calculations and various kinds of controls for operating the ophthalmologic apparatus 1. The computer 100 includes one or more processors and one or more storage devices. Examples of the storage devices include a random access memory (RAM), a read only memory (ROM), a hard disk drive (HDD), and a solid state drive (SSD). Various kinds of computer programs are stored in the storage devices, and the calculations and controls according to the present example are realized through the operations of the processor(s) executed based on the computer programs.

FIG. 2 shows an example of the configuration of the computer 100. The computer 100 includes the examination processor 110, the display processor 120, the illumination intensity changing processor 130, and the alignment processor 140.

The examination processor 110 executes the processing (e.g., calculations and controls) relating to the examination performed by the ophthalmologic apparatus 1. The examination processor 110 is realized by cooperation of hardware including a processor and examination processing software.

The examination processor 110 controls, for example, each of the illumination light source 11, the excitation filter movement mechanism 13A, the interference photographing camera 23, the barrier filter movement mechanism 31A, and the anterior eye segment photographing camera 33.

The controls of the illumination light source 11 include, for example, turning on and off, changing the output light amount, and changing the output wavelength range (wavelength band). The controls of the excitation filter movement mechanism 13A include, for example, the insertion of the excitation filter 13 into the optical path and the removal of the excitation filter 13 from the optical path.

The controls of the interference photographing camera 23 include, for example, the exposure adjustment, the gain adjustment, the detection rate adjustment, and the selection of the detection wavelength range (e.g., the selection of an image sensor to be used). Note that when the diaphragm 21 is a variable diaphragm, the examination processor 110 can control the diaphragm 21.

The controls of the barrier filter movement mechanism 31A include, for example, the insertion of the barrier filter 31 into the optical path and the removal of the barrier filter 31 from the optical path. The controls of the anterior eye segment photographing camera 33 include, for example, the exposure adjustment, the gain adjustment, and the detection rate adjustment.

Furthermore, the examination processor 110 can perform processing and calculations relating to an interference image obtained by the interference photographing camera 23. For example, the examination processor 110 can construct a processed image from a raw image acquired by the interference photographing system 20. The processed image may be, for example, a color map that represents a parameter distribution obtained from a raw image in pseudo colors r a map that represents a region where parameter values belong to a predetermined range. This parameter may be, for example, the thickness of any one of the lipid layer, the aqueous layer and the mucinous layer of the tear film, the thickness of any two layers, or the thickness of the three layers. Further, the processed image may be created by applying any kind of image processing such as correction, adjustment or enhancement, to the raw image.

In addition, the examination processor 110 may be configured to execute the processing disclosed in any of Japanese Unexamined Patent Application Publication No, 1997-289970, Japanese Unexamined Patent Application Publication No. 2001-309889, Japanese Unexamined Patent Application Publication No. 2005-211173, and Japanese Unexamined Patent Application Publication No. 2017-136212, or other known processing. For example, the examination processor 110 may be capable of executing any one or more of the followings: specification of a time-dependent change in the hue of an interference image (i.e., the hue of an interference pattern); evaluation of the degree of progress of dry eye syndrome on the basis of an interference pattern of a color component; evaluation of the location of a dry spot; evaluation of the shape of a dry spot; and evaluation of the direction of the movement of tears around the dry spot.

The examination processor 110 is capable of executing processing and calculations relating to an anterior eye segment image obtained by the anterior eye segment photographing camera 33. For example, the examination processor 110 can construct a processed image from a raw image acquired by the anterior eye segment photographing system 30. As described above, the processed image may be created by applying any kind of image processing such as correction, adjustment or enhancement, to the raw image.

The display processor 120 executes processing for displaying information on the display device 80. The display processor 120 is realized by cooperation of hardware including a processor and display processing software.

For example, in order to display the second information over the first information, the display processor 120 executes, for example, the control of presenting the second layer on the first layer, the control of displaying the first information on the first layer, and the control of displaying the second information on the second layer. Alternatively, the display processor 120 may execute the processing of composing the first information and the second information (e.g., the processing of embedding the second information into the first information), and the processing of displaying the composite information thereby obtained.

The illumination intensity changing processor 130 executes processing for changing the intensity of the illumination light projected onto the anterior eye segment Ea by the illumination system 10. The illumination intensity changing processor 130 is realized by cooperation of hardware including a processor and illumination intensity changing processing software.

In the case where the variable filter 14 is used for changing the illumination intensity, the illumination intensity changing processor 130 executes, for example, the control for changing the filter characteristic of the variable filter 14, or the control for placing one of two or more filters in the optical path.

When changing the intensity of the illumination light projected onto the anterior eye segment Ea by changing any one or both of the intensity and the wavelength band of the illumination light output by the illumination light source (11), the illumination intensity changing processor 130 executes the control of the Illumination light source (11).

The illumination intensity changing processor 130 executes the control for changing the illumination intensity according to a signal sent from the operation device 90, for example. In other words, the ophthalmologic apparatus 1 may be configured so that the illumination intensity can be manually changed. Here, the operation device 90 is operated by the examiner or the subject. It should be noted that the variable range of the illumination intensity can be set in advance to a range appropriate to at least one of the interference photographing and the anterior eye segment photographing.

In the case of automatically changing the illumination intensity, for example, the illumination intensity changing processor 130 may be configured to acquire information on the illumination intensity applied to the subject (i.e., the subject's eye E) in the past examination from medical information (e.g., an electronic medical record) associated with the subject, and to reproduce the illumination intensity acquired.

As another example in the case of automatic change of the illumination intensity, the illumination intensity changing processor 130 may be configured to cause the ophthalmologic apparatus 1 to output visual information or auditory information for inquiring of the subject the degree of glare when the illumination light is projected onto the anterior eye segment Ea, and to control the illumination intensity according to the subject's response to the inquiry.

As yet another example in the case of automatically changing the illumination intensity, the illumination intensity changing processor 130 may be configured to regulate the illumination intensity based on a biosignal of the subject when the illumination light is being projected onto the anterior eye segment Ea. This biosignal may be, for example, any of miosis neural oscillations (or brainwaves), heart rate, perspiration, facial expression and other signals. For example, the ophthalmologic apparatus 1 includes a device for detecting any of the biosignals or is connected to the device. Miosis can be detected, for example, using the anterior eye segment photographing camera 33 and the illumination intensity changing processor 130. Neural oscillations can be detected by using an electroencephalograph (EEG), for example. The heart rate can be detected, for example, by an electrocardiograph (ECG) or a pulse oximeter. Perspiration can be detected by a perspiration meter, for example. The facial expression can be detected, for example, by a camera and the illumination intensity changing processor 130. A biosignal different from the above examples can be detected using a corresponding device.

The alignment processor 140 executes processing relating to the position adjustment (alignment) of the optical system with respect to the subject's eye E. The alignment processor 140 is realized by cooperation of hardware including a processor and alignment processing software.

In addition to the Z alignment, the ophthalmologic apparatus 1 may be capable of performing alignment in the X direction and the Y direction (i.e., XY alignment). The alignment processor 140 executes processing relating to the Z alignment and processing relating to the XY alignment.

First, the processing relating to the Z alignment will be described. The alignment processor 140 can execute the controls of the alignment light source 61 and the controls of the image sensor 62. The controls of the alignment light source include turning on and off, adjusting the light amount, and adjusting the diaphragm, and other controls. The controls of the image sensor 62 include the exposure adjustment, the gain adjustment, the detection rate adjustment, and other controls.

Furthermore, the alignment processor 140 captures a signal output from the image sensor 62, and specifies the projection position of the light on the photo-detection surface of the image sensor 62 based on the signal captured. The alignment processor 140 determines the position of the corneal apex of the subject's eye E based on the projection position specified, and controls the unit movement mechanism 70 on the basis of the determined position to move the examination unit 2 in the front direction and/or the back direction (Z alignment).

Next, the XY alignment will be described. The ophthalmologic apparatus 1 may be configured to perform the XY alignment based on an anterior eye segment image acquired by the anterior eye segment photographing system 30.

For example, the alignment processor 140 analyzes the acquired anterior eye segment image to detect a feature point such as the pupil center or the center of gravity of the pupil. Next, the alignment processor 140 calculates the deviation of the feature point from a predetermined position of the frame (e.g., from the center of the frame) of the anterior eye segment image. Subsequently, the alignment processor 140 controls the unit movement mechanism 70 to move the examination unit 2 in the horizontal direction and/or the vertical direction so as to cancel the calculated deviation (the XY alignment). As a result, the XY alignment can be performed so that the feature point of the anterior eye segment is represented at the predetermined position of the frame.

The computer 100 may include an element different from those shown in FIG. 2. For example, the computer 100 may include a communication interface. The communication interface has a function for communicating with an external device (not shown in the figures). The external device may be one or more of any type of ophthalmologic apparatus, a device that reads information from a recording medium (i.e., a reader device), and a device that writes information into a recording medium (i.e., a writer device), for example. Further, the external device may be one or more of any type of information processing device such as a hospital information system (HIS) server, a digital imaging and communication in medicine (DICOM) server, a doctor's terminal, a mobile terminal, a personal terminal, a cloud server, and other devices.

<Operation>

Figure 4:
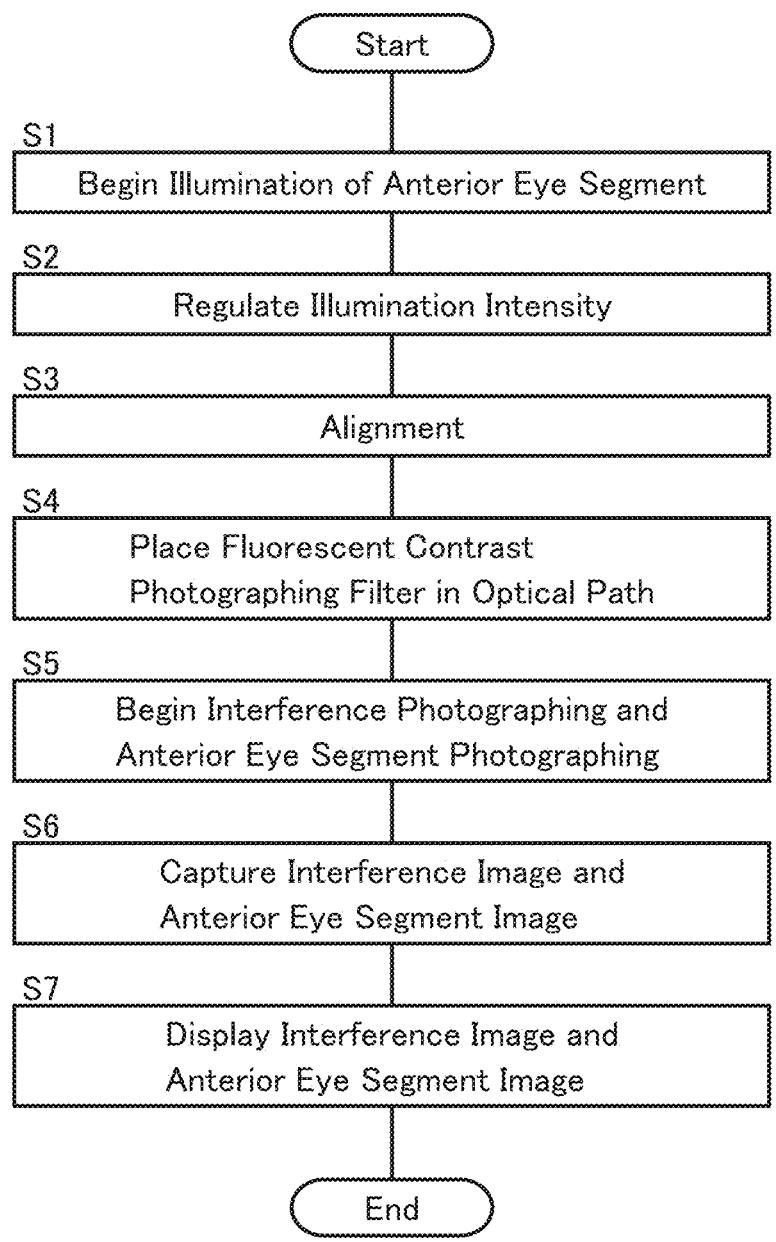
FIG. 4 is a flowchart illustrating an example of the operation of the ophthalmologic apparatus according to the exemplary embodiment.

The operation of the ophthalmologic apparatus 1 according to the present embodiment will be described. FIG. 4 shows an example of the operation of the ophthalmologic apparatus 1.

(S1: Start Illumination of Anterior Eye Segment)

First, the illumination light source 11 is turned on and the illumination light is projected onto the anterior eye segment Ea.

(S2: Regulate Illumination Intensity)

Next, the intensity of the illumination light projected onto the anterior eye segment Ea is regulated by controlling the variable filter 14 or other control. The illumination intensity can be regulated, for example, in the manner described above.

(S3: Alignment)

Alignment is then performed. In the present embodiment, for example, the Z alignment is performed after the XY alignment. The XY alignment and the Z alignment can be performed, for example, in the manner described above.

(S4: Place Fluorescent Contrast Photographing Filter in Optical Path)

Next, the excitation filter 13 and the barrier filter 31 are respectively placed in the corresponding optical paths.

(S5: Begin Interference Photographing and Anterior Eye Segment Photographing)

When the above preparation is completed, the interference photographing by the interference photographing system 20 and the anterior eye segment photographing by the anterior eye segment photographing system 30 are begun.

The interference photographing is performed to photograph an interference pattern representing the state of tears on the cornea Ec such as the thickness distribution of the tears. The interference photographing is performed over a preset period, for example. Alternatively, the interference photographing is performed until the state of the tears on the cornea Ec reaches a predetermined state (e.g., until the tear film breakup has progressed up to a sufficient degree).

For example, the anterior eye segment photographing is performed during at least part of the execution period of the interference photographing. This makes it possible to obtain an anterior eye segment image whose acquisition time is substantially the same as that of a certain interference image obtained by the interference photographing. When the anterior eye segment photographing is performed throughout the entire execution period of the interference photographing, as in the case where the interference photographing and the anterior eye segment photographing are performed in parallel, it is possible to obtain anterior eye segment images temporally corresponding to respective interference images acquired by the interference photographing.

The timings of the interference photographing and those of the anterior eye segment photographing can synchronized with each other. For example, the interference photographing and the anterior eye segment photographing can be performed at the same repetition timings (e.g., the same imaging rate, the same frame rate).

(S6: Capture Interference Image and Anterior Eye Segment Image)

For example, the display processor 120 captures an interference image and an anterior eye segment image acquired almost simultaneously with each other. Alternatively, the display processor 120 may capture an interference image and an anterior eye segment image acquired at substantially different timings from each other.

(S7: Overlay Interference Image on Anterior Eye Segment Image)

The display processor 120 displays the interference image and the anterior eye segment image captured in step S6 on the display device 80. In the present example, the display processor 120 displays the interference image over the anterior eye segment image.

When an interference image and an anterior eye segment image acquired almost simultaneously with each other are captured in step S6, the ophthalmologic apparatus 1 can overlay the interference image on the anterior eye segment images without performing registration between these images.

On the other hand, when an interference image and an anterior eye segment image acquired at substantially different timings from each other are captured in step S6, it is desirable for the ophthalmologic apparatus 1 to perform registration between these images. However, the contents represented in the interference image and the contents represented in the anterior eye segment image are different from each other, and thus, it is difficult to carry out registration between these images through direct comparison of these images.

Therefore, apart from the anterior eye segment image to be displayed, another anterior eye segment image (referred to as a supplementary anterior eye segment image) acquired almost simultaneously with the interference image is used. The selection of the supplementary anterior eye segment image can be performed based on, for example, the synchronization between the interference photographing and anterior eye segment photographing described above. The display processor 120 can execute registration between the anterior eye segment image to be displayed and the supplementary anterior eye segment image, to determine the deviation of the supplementary anterior eye segment image with respect to the anterior eye segment image to be displayed. Further, the display processor 120 can perform registration between the interference image and the anterior eye segment image to be displayed so that the deviation determined is canceled. This terminates the present operation example (end).

<Modification Example>

The above embodiment performs the Z alignment using the optical lever and the XY alignment using the anterior eye segment image. The following describes an example of an alignment method applicable to some embodiments instead of the Z alignment and the XY alignment.

Figure 5A:
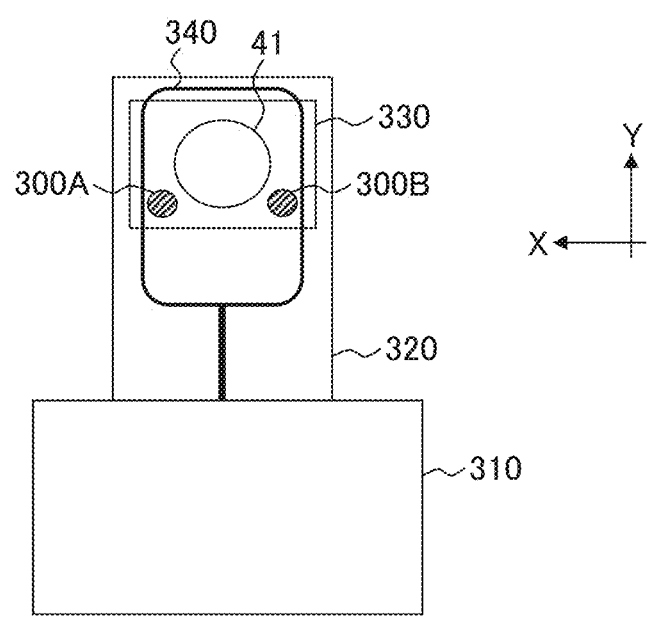
FIG. 5A is a schematic diagram illustrating an example of the configuration of an ophthalmologic apparatus according to a modification example.
Figure 5B:
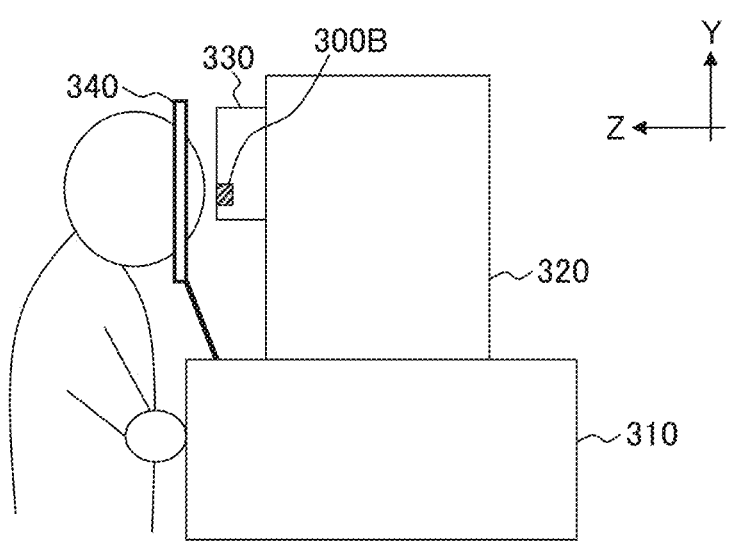
FIG. 5B is a schematic diagram illustrating an example of the configuration of the ophthalmologic apparatus according to the modification example.
Figure 6:
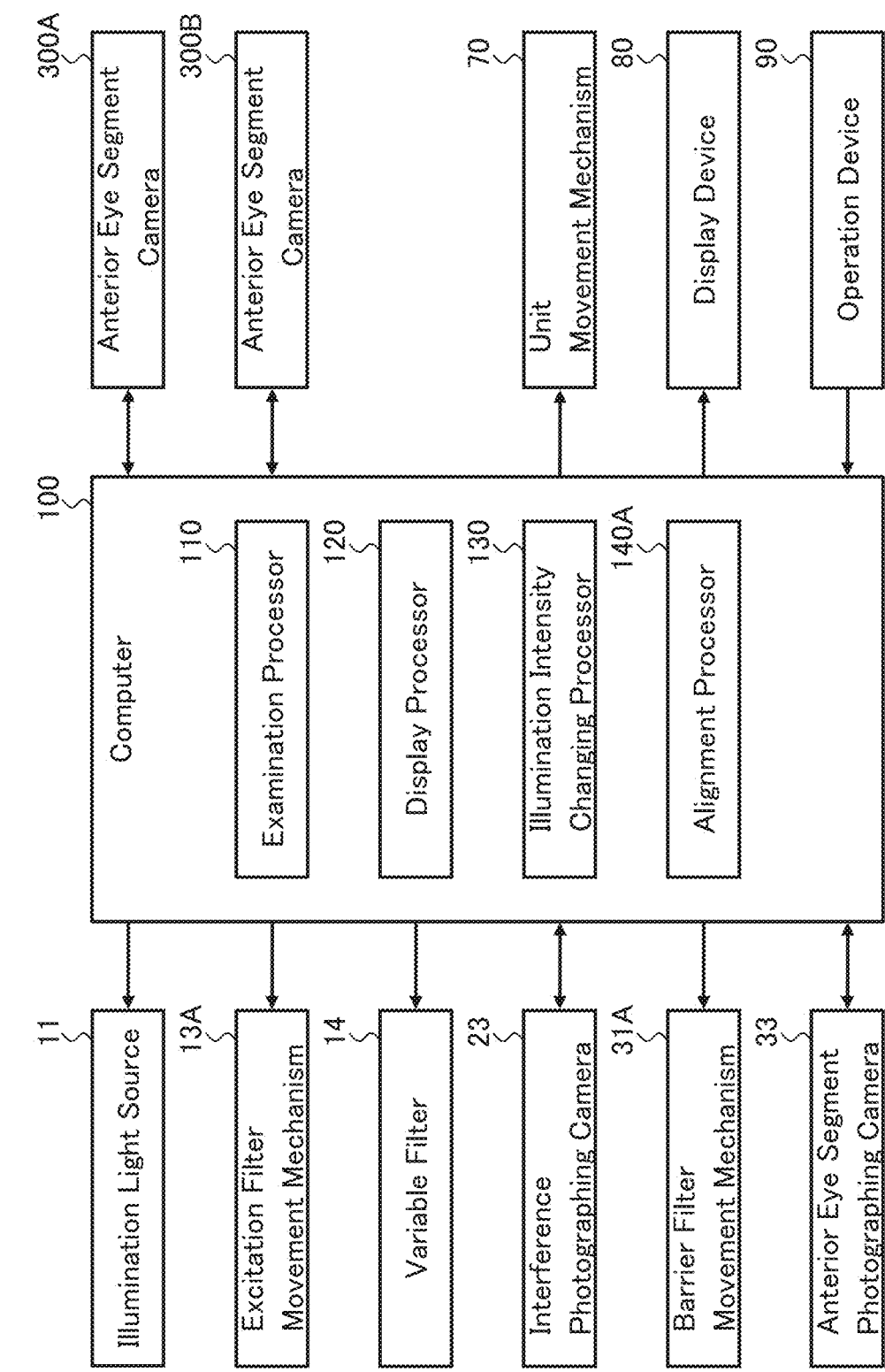
FIG. 6 is a schematic diagram illustrating an example of the configuration of the ophthalmologic apparatus according to the modification example.

The present modification example performs three dimensional alignment (XYZ alignment) based on two or more photographed images obtained by photographing the anterior eye segment Ea from directions different from each other. FIGS. 5A, 5B, and 6 show a configuration example for realizing the XYZ alignment. FIGS. 5A and 5B show an example of the exterior of the ophthalmologic apparatus according to the present modification example. The configuration shown in FIG. 6 can be applied instead of the configuration shown in FIG. 2.

For example, the configurations of the ophthalmologic apparatus according to the present modification example may be the same as those of the ophthalmologic apparatus 1 of the above embodiment, except for the following points: in that the two anterior eye segment cameras 300A and 300B are provided; in that the alignment processor 140A is provided in place of the alignment processor 140; and in that the alignment light source 61 and the image sensor 62 are not included. However, the ophthalmologic apparatus according to the present modification may include the alignment light source 61 and the image sensor 62. In the following description, the same reference symbols as those of the ophthalmologic apparatus 1 are used unless otherwise mentioned.

The ophthalmologic apparatus according to the modification example has a chin rest and a forehead rest for supporting the face of the subject. The same may apply to the ophthalmologic apparatus 1 of the above embodiment.

The base 310 stores a driving system and a processing system. For example, the base 310 stores the unit movement mechanism 70 and the computer 100 shown in FIG. 1.

The housing 320 provided on the base 310 stores an optical system and a driving system. For example, the housing 320 stores the examination unit 2 shown in FIG. 1.

The lens container 330 is provided in such a way that it protrudes from the front surface of the housing 320, and accommodates at least the lens 41.

The display device 80 shown in FIG. 1 may be provided on the housing 320. Further, the operation device 90 may be provided on at least one of the base 310 and the housing 320.

The two anterior eye segment cameras 300A and 300B are provided on the front surface of the housing 320. The two anterior eye segment cameras 300A and 300B photograph the anterior eye segment Ea of the subject's eye E from two directions different from each other (i.e., from two positions different from each other).

Each of the two anterior eye segment cameras 300A and 300B includes an image sensor such as a CCD image sensor or a CMOS image sensor. In the present modification example, the two anterior eye segment cameras 300A and 300B are provided on the surface of the housing 320 that faces the subject. As shown in FIG. 5A, the two anterior eye segment cameras 300A and 300B are provided at positions outside the optical path that passes through the lens 41.

Although the present modification example includes the two anterior eye segment cameras 300A and 300B, the number of anterior eye segment cameras provided may be two or more. Note that, in consideration of the processing load of calculation for three dimensional alignment, it is sufficient as long as the anterior eye segment can be photographed from two directions different from each other (but not limited to this). Alternatively, a movable anterior eye segment camera may be provided. The movable anterior eye segment camera can perform the anterior eye segment photographing from two or more positions different from one another, in turn.

Although the present modification example is provided with the two anterior eye segment cameras 300A and 300B separately from the anterior eye segment photographing system 30, one of two or more anterior eye segment cameras may be the anterior eye segment photographing system 30 in some embodiments.

When two or more anterior eye segment cameras are provided, the ophthalmologic apparatus can photograph an anterior eye segment from two or more directions different from one another in a substantially simultaneous manner. "Substantially simultaneous" refers to, as well as the case where photographing timings by two or more anterior eye segment cameras are simultaneous, a case where a time lag exists between the photographing timings, wherein the time lag is to the extent that eye movement can be ignored, for example. By performing such substantially simultaneous photographing, the ophthalmologic apparatus can acquire two or more anterior eye segment images when the subject's eye is substantially at the same position and orientation.

The photographing with two or more anterior eye segment cameras may be either moving image photographing or still image photographing. In the case of the moving image photographing, the above substantially simultaneous anterior eye segment photographing can be realized by the control of matching the respective photographing start timings or by the control of the respective frame rates or respective photographing timings of frames. On the other hand, in the case of the still image photographing, substantially simultaneous anterior eye segment photographing can be realized by the control of matching the respective photographing timings.

The two anterior eye segment images acquired substantially simultaneously by the two anterior eye segment cameras 300A and 300B are sent to the computer 100.

The alignment processor 140A analyzes the two photographed images (the anterior eye segment images) substantially simultaneously acquired by the two anterior eye segment cameras 300A and 300B, to determine the three dimensional position of the subject's eye E.

This analysis may include, for example, the specification of a feature position and the calculation of the three dimensional position thereof, as disclosed in U.S. Patent Application Publication No. 2015/0085252 A1. Prior to these processes, the ophthalmologic apparatus may execute processing for correcting the distortion of the photographed image obtained by each of the two anterior eye segment cameras 300A and 300B.

In the specification of the feature position, the alignment processor 140A analyzes each of the two anterior eye segment images acquired substantially simultaneously by the two anterior eye segment cameras 300A and 300B, for example, to specify a position (referred to as a feature position) in each photographed image corresponding to a predetermined feature site of the anterior eye segment Ea. The feature site is typically the pupil center (or the center of gravity of the pupil).

In order to specify the position of the center of the pupil, the alignment processor 140A first specifies an image region corresponding to the pupil of the subject's eye E (a pupil region), based on the distribution of the pixel values (e.g., brightness values) of the photographed image. Generally, the pupil is depicted with lower brightness than other sites. Therefore, the pupil region can be specified by searching for a low brightness image region. In this process, the pupil region may be specified in consideration of the shape of the pupil. More specifically, the alignment processor 140A may be configured to specify the pupil region by searching for an image region of substantially circular shape and low brightness.

Next, the alignment processor 140A specifies the center position of the pupil region specified. As described above, the pupil is substantially circular shape. Therefore, the alignment processor 140A can specify the contour of the pupil region, specify the center position of the contour (or specify the center position of an approximate circle or an approximate ellipse of the contour), and set the specified center position to the pupil center.

In the calculation of the three dimensional position, the alignment processor 140A calculates the three dimensional position of the feature site of the subject's eye E, based on the respective positions of the two anterior eye segment cameras 300A and 300B and the feature positions in the two photographed images specified by the above processes. This calculation is carried out using trigonometry, as described in U.S. Patent Application Publication No. 2015/0085252 A1.

Based on the three dimensional position of the subject's eye E calculated in this manner, the alignment processor 140A controls the unit movement mechanism 70 so that the optical axis of the optical system matches the axis of the subject's eye E, and controls the unit movement mechanism 70 so that the distance between the subject's eye E and the optical system matches a predetermined working distance. Here, the former process corresponds to the XY alignment and the latter process corresponds to the Z alignment.

<Actions and Effects>

Some actions and effects of the ophthalmologic apparatus according to some exemplary embodiments will be described below.

The ophthalmologic apparatus according to some exemplary embodiments includes an illumination system, an interference photographing system, an anterior eye segment photographing system, a first optical path coupling element, and a controller.

The illumination system is configured to project illumination light output from a light source, onto an anterior eye segment of a subject's eye. In the above example aspect, the illumination system 10 corresponds to the illumination system. The illumination system 10 is configured to project the illumination light output from the illumination light source 11 onto the anterior eye segment Ea.

The interference photographing system is configured to photograph an interference pattern formed on the cornea by the illumination light that projected onto the anterior eye segment by the illumination system. In the above example aspect, the interference photographing system 20 corresponds to the interference photographing system. The interference photographing system 20 acquires an interference image by photographing the interference pattern formed on the cornea Ec by the illumination light that is projected onto the anterior eye segment Ea by the illumination system 10.

The anterior eye segment photographing system is configured to photograph the anterior eye segment onto which the illumination light is being projected by the illumination system. In the above example aspect, the anterior eye segment photographing system 30 corresponds to the anterior eye segment photographing system. The anterior eye segment photographing system 30 photographs the anterior eye segment Ea onto which the illumination light is projected by the illumination system 10. The anterior eye segment photographing system 30 is configured to photograph a wide area of the anterior eye segment Ea from the front.

The first optical path coupling element configured to couple the optical path of the interference photographing system and the optical path of the anterior eye segment photographing system with one another. In the above example aspect, the optical path coupling element 51 corresponds to the first optical path coupling element. The optical path coupling element 51 is configured to couple the optical path of the interference photographing system 20 and the optical path of the anterior eye segment photographing system 30. Furthermore, the optical path coupling element 51 is configured to couple the optical path of the illumination system 10 and the optical path of the anterior eye segment photographing system 30.

The controller is configured to control a display device to display an interference image acquired by the interference photographing system over an anterior eye segment image acquired by the anterior eye segment photographing system. The displayed interference image may be a raw image acquired by the interference photographing system or a processed image obtained from the raw image. The display device may be an element of the ophthalmologic apparatus or a peripheral device of the ophthalmologic apparatus.

In the above example aspect, the computer 100 (particularly the display processor 120) corresponds to the controller. The computer 100 is configured to display the interference image acquired by the interference photographing system 20 over the anterior eye segment image acquired by the anterior eye segment photographing system 30, on the display device 80.

According to the exemplary embodiments thus configured, the interference photographing system and the anterior eye segment photographing system are separately provided, and their optical paths are coupled with one another by the first optical path coupling element. Therefore, the ophthalmologic apparatus can perform the interference photographing and the anterior eye segment photographing almost at the same time. This makes it possible to reduce the possibility of occurrence of positional deviation (misregistration) between the interference image and the anterior eye segment image caused by eye movements and body movements.

Furthermore, according to the exemplary embodiments, the ophthalmologic apparatus can photograph a wide area of the anterior eye segments by the anterior eye segment photographing system provided separately from the interference photographing system. This makes it possible to reduce the possibility of overlooking an abnormality occurring in the periphery or edge of the cornea, and to perform the examination in an efficient manner.

In addition, according to the exemplary embodiments, the ophthalmologic apparatus can overlay the interference image representing the state of tears on the anterior eye segment image. Therefore, the locations of the abnormalities of tears or the distribution of the abnormalities can be overlaid on the anterior eye segment image. As a result, the ophthalmologic apparatus can present the abnormality occurrence locations to the user in a manner which the user can easily (intuitively) grasp the abnormality occurrence locations.

As described above, according to the exemplary embodiments, the ophthalmologic apparatus can present the abnormality occurrence locations of the state of tears over a wide area of the anterior eye segment with good locational precision.

The ophthalmologic apparatus according to some exemplary embodiments may further include a first lens group disposed in a position between the subject's eye and the first optical path coupling element and a second lens group disposed in a position on an opposite side of the subject's eye with respect to the first optical path coupling element. Here, a combination of the first lens group and the second lens group may be configured to function as an objective lens of the interference photographing system, and the first lens group may be configured to function as an objective lens of the anterior eye segment photographing system.

In the above example aspect, the two lenses 41 and 42 correspond to the first lens group, and the two lenses 43 and 44 correspond to the second lens group. Furthermore, the four lenses 41 to 44 function as the objective lens of the interference photographing system 22, and the two lenses 41 and 42 function as the objective lens of the anterior eye segment photographing system 30.

In some exemplary embodiments, a lens located closest to the first optical path coupling element among lenses included in the anterior eye segment photographing system, may be located at or near the focal position of the first lens group.

In the above example aspect, the lens located closest to the optical path coupling element 51 among the lenses 32 included in the anterior eye segment photographing system 30, is located at or near the focal position of the first lens group consisting of the two lenses 41 and 42.

According to the exemplary embodiments thus configured, at least the following two effects are achieved. Firstly, regarding the interference photographing system, the ophthalmologic apparatus can make the illumination light incident substantially perpendicularly to each position on the cornea. In addition, the ophthalmologic apparatus can detect the reflected light from each position on the cornea that travels, in the opposite direction, along substantially the same route as the incident path of the illumination light to the each corresponding position. This makes the path of the illumination light corresponding to each position on the cornea and the path of the reflected light thereof substantially matched. As a result, the ophthalmologic apparatus can detect the distribution of the state of tears on the curved surface of the cornea, from the directions perpendicular to the curved surface.

Secondly, regarding the anterior eye segment photographing system, the anterior eye segment photographing system can be disposed near the first optical path coupling element, and further the anterior eye segment photographing system (lens therein) can be disposed at or near the back focal position of the first lens group. This makes it possible to widen the field of view of the anterior eye segment photographing system.

The ophthalmologic apparatus according to some exemplary embodiments may further include a second optical path coupling element that couples the optical path of the illumination system and the optical path of the interference photographing system with one another. In the above example aspect, the optical path coupling element 53 corresponds to the second optical path coupling element. The optical path coupling element 53 is configured to couple the optical path of the illumination system 10 and the optical path of the interference photographing system 20.

In some exemplary embodiments, each of the first optical path coupling element and the second optical path coupling element may be a beam splitter. Further, and returning light of the illumination light for photographing the interference pattern may be reflected by each of the first optical path coupling element and the second optical path coupling element, and guided to an image sensor of the interference photographing system.

In the above example aspect, each of the optical path coupling element 51 and the optical path coupling element 53 is a beam splitter (e.g., a half mirror etc.). Further, the returning light of the illumination light for photographing the interference pattern may be reflected by each of the optical path coupling element 51 and the optical path coupling element 53, and guided to the interference photographing camera 23 corresponding to the image sensor.

According to the exemplary embodiment thus configured, the disturbance of light when passing through a beam splitter can be avoided while reducing the size of the p al system. Therefore, it becomes possible to detect the interference pattern generated on the cornea with high accuracy.

The ophthalmologic apparatus according to some exemplary embodiments may further include an illumination intensity changing device that changes the intensity of the illumination light projected onto the anterior eye segment. In the above example aspect, the variable filter 14 and the illumination intensity changing processor 130 correspond to the illumination intensity changing device.

According to the exemplary embodiment configured in this way, the ophthalmologic apparatus can perform the examination with the light of suitable intensity. For example, the ophthalmologic apparatus can reduce the possibility that the subject closes his or her eyes due to glare during the examination that takes a certain period of time, such as the tear film breakup time (BUT) examination. In addition, the ophthalmologic apparatus can reduce a burden on the subject.

The ophthalmologic apparatus according to some exemplary embodiments may further include an excitation filter that generates excitation light for a fluorescent agent administered to the anterior eye segment from the illumination light, and a barrier filter that selectively passes fluorescence emitted from the fluorescent agent that has absorbed the excitation light. In the above example aspect, the excitation filter 13 corresponds to the excitation filter, and the barrier filter 31 corresponds to the barrier filter.

According to the exemplary embodiment configured in this way, the fluorescent contrast photographing of the anterior eye segment can be performed. Therefore, the examiner can observe the state of the cornea and the state of the tears in more detail.

The ophthalmologic apparatus according to some exemplary embodiments may include elements for alignment. The alignment can facilitates the examination. Some examples of the configuration for alignment are given below.

As the first example, the ophthalmologic apparatus according to some exemplary embodiments may include a projection system, a detection system, and a first alignment device. The projection system is configured to project alignment light onto the anterior eye segment along a direction non-parallel to the optical axis of the optical path from the first optical path coupling element toward the subject's eye. The detection system is configured to detect reflected light of the alignment light projected onto the anterior eye segment by the projection system. The first alignment device is configured to perform alignment in a direction along the optical axis, based on an output from the detection system.

In the above example aspect, the alignment light source 61, the lens 42, and the lens 41 correspond to the projection system. Furthermore, the lens 41, the lens 42, and the image sensor 62 correspond to the detection system. In addition, the unit movement mechanism 70 and the alignment processor 140 correspond to the first alignment device. The Z alignment is carried out using these elements.

In the first example, the projection system may include an alignment light source that outputs the alignment light. Further, the detection system may include an image sensor that detects the reflected light of the alignment light. In addition, the alignment light source and the image sensor may be disposed in positions on the opposite side of the subject's eye with respect to the first optical path coupling element.

In the above example aspect, the alignment light source 61 corresponds to the alignment light source and the image sensor 62 corresponds to the image sensor. Further, the alignment light source 61 and the image sensor 62 are disposed in positions on the opposite side of the subject's eye E with respect to the optical path coupling element 51, that is, on the side of the anterior eye segment photographing system 30. The optical path coupling element 51 is formed with a notch, an aperture, a light transmitting part, or the like, and the light may pass through the optical path coupling element 51 via the notch, the aperture, the light transmitting part, or the like.

As the second example, the ophthalmologic apparatus according to some exemplary embodiments may further include a second alignment device. The second alignment device is configured to perform alignment in a direction perpendicular to the optical axis of the optical path from the first optical path coupling element toward the subject's eye, based on an anterior eye segment image acquired by the anterior eye segment photographing system.

In the above example aspect, the unit movement mechanism 70 and the alignment processor 140 correspond to the second alignment device. The XY alignment is carried out using these elements.

As the third example, the ophthalmologic apparatus according to some exemplary embodiments includes two or more photographing devices and a third alignment device. The two or more photographing devices are configured to photograph the anterior eye segment from directions different from each other. The third alignment device is configured to perform three dimensional alignment based on two or more photographed images respectively acquired by the two or more photographing devices.

In the above example aspect, the two anterior eye segment cameras 300A and 300B correspond to the two or more photographing devices, and the unit movement mechanism 70 and the alignment processor 140A correspond to the third alignment device. The three dimensional alignment (the XYZ alignment) is carried out using these elements.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

In this specification, the term "and/or" includes any and all combinations of one or more of the associated listed items.

Singular forms in this specification are intended to include the plural forms as well, unless the context clearly indicates otherwise.

The terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

In this specification, ordinal numbers (e.g., first and second) used to describe elements are only intended to distinguish one element from another element.

What is claimed is:

1. An ophthalmologic apparatus comprising:
   an illumination system that projects illumination light output from a light source onto an anterior eye segment of a subject's eye;
   an interference photographing system for photographing an interference pattern formed by a tear film on a cornea by the illumination light;
   an anterior eye segment photographing system for photographing the anterior eye segment onto which the illumination light is being projected;
   a first optical path coupling element that couples an optical path of the interference photographing system and an optical path of the anterior eye segment photographing system with one another; and
   a controller that controls a display device to display an interference image of the tear film acquired by the interference photographing system over an anterior eye segment image acquired by the anterior eye segment photographing system.

2. The ophthalmologic apparatus of claim 1, further comprising:
   a first lens group disposed in a position between the subject's eye and the first optical path coupling element; and
   a second lens group disposed in a position on an opposite side of the subject's eye with respect to the first optical path coupling element, wherein
   a combination of the first lens group and the second lens group functions as an objective lens of the interference photographing system, and
   the first lens group functions as an objective lens of the anterior eye segment photographing system.

3. The ophthalmologic apparatus of claim 2, wherein a lens located closest to the first optical path coupling element among lenses included in the anterior eye segment photographing system is disposed at a focal position of the first lens group or in a vicinity thereof.

4. The ophthalmologic apparatus of claim 1, further comprising a second optical path coupling element that couples an optical path of the illumination system and the optical path of the interference photographing system with one another.

5. The ophthalmologic apparatus of claim 4, wherein
   each of the first optical path coupling element and the second optical path coupling element is a beam splitter, and
   returning light of the illumination light for photographing the interference pattern is reflected by each of the first optical path coupling element and the second optical path coupling element and guided to an image sensor of the interference photographing system.

6. The ophthalmologic apparatus of claim 1, further comprising an illumination intensity changing device that changes an intensity of the illumination light projected onto the anterior eye segment.

7. The ophthalmologic apparatus of claim 1, further comprising:
   an excitation filter that generates excitation light for a fluorescent agent administered to the anterior eye segment from the illumination light; and
   a barrier filter that selectively passes fluorescence emitted from the fluorescent agent that has absorbed the excitation light.

8. The ophthalmologic apparatus of claim 1, further comprising:
- a projection system that projects alignment light onto the anterior eye segment along a direction non-parallel to an optical axis of an optical path from the first optical path coupling element toward the subject's eye;
- a detection system that detects reflected light of the alignment light from the anterior eye segment; and
- a first alignment device that performs alignment in a direction along the optical axis based on an output from the detection system.

9. The ophthalmologic apparatus of claim 8, wherein
the projection system comprises an alignment light source that outputs the alignment light,
the detection system comprises an image sensor that detects the reflected light, and
the alignment light source and the image sensor are disposed in positions on an opposite side of the subject's eye with respect to the first optical path coupling element.

10. The ophthalmologic apparatus of claim 1, further comprising a second alignment device that performs alignment in a direction perpendicular to the optical axis of the optical path from the first optical path coupling element toward the subject's eye, based on an anterior eye segment image acquired by the anterior eye segment photographing system.

11. The ophthalmologic apparatus of claim 1, further comprising:
- two or more photographing devices that photograph the anterior eye segment from directions different from each other, and
- a third alignment device that performs three dimensional alignment based on two or more photographed images respectively acquired by the two or more photographing devices.

12. The ophthalmologic apparatus of claim 1, wherein the controller is further configured to display the interference image indicating a thickness of at least a portion of the tear film.

13. The ophthalmologic apparatus of claim 1, wherein the controller is further configured to display the interference image including a color map that represents a distribution of a parameter indicating a thickness of at least one of a lipid layer, an aqueous layer, and a mucinous layer of the tear film.

* * * * *